(12) United States Patent
Han

(10) Patent No.: US 11,378,503 B2
(45) Date of Patent: Jul. 5, 2022

(54) NUMERICAL MODELING OF LASER PERFORATING PROCESS

(71) Applicant: Saudi Arabian Oil Company, Dhahran (SA)

(72) Inventor: Yanhui Han, Katy, TX (US)

(73) Assignee: Saudi Arabian Oil Company, Dhahran (SA)

(*) Notice: Subject to any disclaimer, the term of this patent is extended or adjusted under 35 U.S.C. 154(b) by 800 days.

(21) Appl. No.: 16/277,547

(22) Filed: Feb. 15, 2019

(65) Prior Publication Data

US 2019/0257729 A1 Aug. 22, 2019

Related U.S. Application Data

(60) Provisional application No. 62/710,407, filed on Feb. 16, 2018.

(51) Int. Cl.
*G01N 3/60* (2006.01)
*G01N 33/24* (2006.01)
*B23K 26/06* (2014.01)
*G01V 99/00* (2009.01)
*B23K 31/12* (2006.01)
*B23K 26/402* (2014.01)
(Continued)

(52) U.S. Cl.
CPC .............. *G01N 3/60* (2013.01); *B23K 26/06* (2013.01); *B23K 26/38* (2013.01); *B23K 26/402* (2013.01); *B23K 31/125* (2013.01); *G01N 33/24* (2013.01); *G01V 99/005* (2013.01); *B23K 2103/50* (2018.08); *E21B 43/119* (2013.01); *G01N 2203/0057* (2013.01)

(58) Field of Classification Search
CPC .......... G01N 3/60; G01N 33/24; B23K 26/06; B23K 26/38; B23K 26/402; B23K 31/125; G01V 99/005
See application file for complete search history.

(56) References Cited

U.S. PATENT DOCUMENTS

2006/0041411 A1 2/2006 Yong et al.
2009/0132218 A1 5/2009 Ledgerwood, III
2018/0322227 A1* 11/2018 Yateem .................. G06F 30/20

FOREIGN PATENT DOCUMENTS

| CN | 102737137 | 10/2012 |
|---|---|---|
| EP | 3752315 | 12/2020 |
| WO | 2015113302 | 8/2015 |

OTHER PUBLICATIONS

EPO Communication Pursuant to Article 94(3) in European Appln. No. 19708745.5, dated Sep. 6, 2021, 5 pages.
(Continued)

*Primary Examiner* — Bryan Bui
(74) *Attorney, Agent, or Firm* — Fish & Richardson P.C.

(57) ABSTRACT

In a general implementation, data regarding a rock sample from a drilling site is received. A thermal-mechanical interaction model is generated based on the rock sample date. The thermal-mechanical interaction model is used to determine a penetration rate and mechanical damage around perforation channels through the modeling of heat that is emitted on an exposed surface of the rock sample by a laser beam emitted from a laser beam source. The determined penetration rate and mechanical damage is used to evaluate an effectiveness of the laser beam source to be used in a perforation at the drilling site.

17 Claims, 13 Drawing Sheets

(51) Int. Cl.
    *B23K 26/38*     (2014.01)
    *E21B 43/119*     (2006.01)
    *B23K 103/00*     (2006.01)

(56) References Cited

OTHER PUBLICATIONS

GCC Examination Report in GCC Appln. No. GC 2019-37059, dated Dec. 9, 2020, 3 pages.
International Search Report and Written Opinion issued in International Application No. PCT/US2019/018469 dated Jul. 16, 2019, 5 pages.
GCC Examination Report in GCC Appln. No. GC 2019-37059, dated May 14, 2020, 3 pages.
Alda, "Laser and Gaussian Beam Propagation and Transformation," Encyclopedia of Optical Engineering, Marcel Dekker, Inc., 2003, 15 pages.
Batarseh et al., "Well Perforation using High Power Laser," SPE 84418, SPE Annual Technical Conference and Exhibition, in Denver, Colorado, Oct. 5-8, 2003, 10 pages.
Bell, "Perforating Underbalance—Evolving Techniques," SPE 13413, Distinguished Author Series, Journal of Petroleum Technology, vol. 36, Issue 10, Oct. 1984, 14 pages.
Gahan et al., "Determination of Enery Required to Remove Rock," SPE 71466, presented at the 2001 SPE Annual Technical Conference and Exhibition, in New Orleans, Louisiana, Sep. 30 -Oct. 3, 2001, 11 pages.
Ganesh et al., "A Generalized Thermal Modeling for Laser Drilling Process—I. Mathematical Modeling and Numerical Methodology," International Journal of Heat and Mass Transfer, vol. 40, Issue 14, Sep. 1997, 10 pages.
Graves and O'Brien, "StarWars Laser Technology Applied to Drilling and Completing Gas Wells," SPE 49259, SPE Annual Technical Conference and Exhibition, Society of Petroleum Engineers, Sep. 27-30, 1998, 10 pages.
Halleck and Behrmann, "Penetration of Shaped Charges in Stressed Rock," the 31st US Symposium on Rock Mechnics (USRMS), American Rock Mechanics Association, Jun. 18-20, 1990, 8 pages.
Han et al., "Numerical Modeling of Thermal-Mechanical Interaction Process in Laser Heating," SPE 183836-MS, presented at the SPE Middle East Oil and Gas Show and Conference, in Manama, Kingdom of Bahrain, Mar. 6-9, 2017, 12 pages.
Itasca, "Three-dimensional Fast Lagrangian Analysis of Continua (FLAC3d)," Version 5.0, Minneapolis, Minnesota, 2011, 20 pages.
Maurer, "Novel Drilling Techniques," New York: Pergamon Press, V114, 1968, 130 pages.
Parker et al., "Laser Drilling: Effects of Beam Application Methods of Improving Rock Removal," SPE 84353, SPE Annual Technical Conference and Exhibition, Society of Petroleum Engineers, Oct. 5-8, 2003, 7 pages.
Verhoeven et al., "Modelling Laser Induced Melting," Mathematical and Computer Modelling, vol. 37, Issue 3-4, 2003, 19 pages.

\* cited by examiner

NUMERICAL MODELING OF LASER PERFORATING PROCESS

CLAIM OF PRIORITY

This application claims priority to U.S. Provisional Application Ser. No. 62/710,407, filed Feb. 16, 2018, the entire contents of which are incorporated here by reference.

TECHNICAL FIELD

This disclosure relates to methods, systems, and apparatus for improving the exploration for hydrocarbons.

BACKGROUND

A perforation is a hole punched in the casing or liner of a well to connect it to a reservoir and create a conductive pathway for fluids to flow between the production well and reservoir formation. In cased hole completions, the well is drilled down past the section of the formation desired for production. A casing or a liner is run to separate the formation from the well bore. Completion of the well can involve running a string of shaped charges down to the desired depth and firing them to perforate the casing or liner. Such perforating techniques, however, may introduce mechanical compaction damage and permeability loss in the rock formations around the perforation channels.

SUMMARY

The present disclosure describes methods and systems, including computer-implemented methods, computer-program products, and computer systems for improving laser heating technics for the perforation of a well.

In a general implementation, data regarding a rock sample from a drilling site is received. A thermal-mechanical interaction model is generated based on the rock sample date. The thermal-mechanical interaction model is used to determine a penetration rate and mechanical damage around perforation channels through the modeling of heat that is emitted on an exposed surface of the rock sample by a laser beam emitted from a laser beam source. The determined penetration rate and mechanical damage is used to evaluate an effectiveness of the laser beam source to be used in a perforation at the drilling site.

Implementations include a thermal-mechanical interaction model employed to capture the heat conduction, thermal-mechanical interaction, and mechanical stressing, deformation and damage processes inside rock samples heated by a high-power laser beam at the top surface of a rock sample, which can be isotropic or anisotropic, homogeneous or heterogeneous. The thermal-mechanical interaction model can predict the penetration progress and mechanical damage around perforation channels created by heating with the laser beam.

The details of one or more implementations of the subject matter of this specification are set forth in the accompanying drawings and the later description. Other features, aspects, and advantages of the subject matter will become apparent from the description, the drawings, and the claims.

DETAILED DESCRIPTION

This disclosure generally describes an optimization methodology for modeling the perforation of well casings or liners use in the exploration of hydrocarbons and other resources located underground. The disclosure is presented to enable any person skilled in the art to make and use the disclosed subject matter in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described or illustrated implementations, but is to be accorded the widest scope consistent with the principles and features disclosed herein.

To reduce or eliminate the mechanical compaction damage and permeability loss in the rock formations around the perforation channels, laser heating technics may be employed to perforate the casing or liner in a wellbore. Perforation using laser heating technics may also prevent mechanical compaction damage, avoid the loss of reservoir hydraulic conductivity, and increase the permeability of the rock sample. Simulation of such laser heating technics through modeling and experimentation can be used to improve the technics and increase their desired results. However, laboratory experiments may be limited to small rock samples, so the influence of heterogeneities and discontinuities in the lasing process may not be suitably tested. Additionally, the mechanical, hydraulic, and thermal loads acting on the rock mass in the reservoir are difficult to duplicate in a laboratory environment.

In view of the forgoing, the described thermal-mechanical interaction system can include three-dimensional modeling of thermal-mechanical-phase change physics in the perforating process, accommodating the absorbed energy in the phase changes of melting and vaporization into temperature-dependent specific heat, a lased-tunnel-evolution algorithm, and a predictive tool, which may be in template form. The described system can be employed to simulate laser heating technics for the perforation of a well. The described system can be employed to predict the penetration progress and mechanical damage around perforation channels created by heating with, for example, a laser beam. The described system can also, for example, simulate the capture of heat conductions and the thermal-mechanical interaction and mechanical stressing of such technics. Moreover, the described system may be use to simulate the heating of rock samples by a high-power laser beam at a top surface where the deformation and damage processes inside each sample can be modeled. Such rock samples may be, for example, isotropic or anisotropic and homogeneous or heterogeneous.

Figure 1:
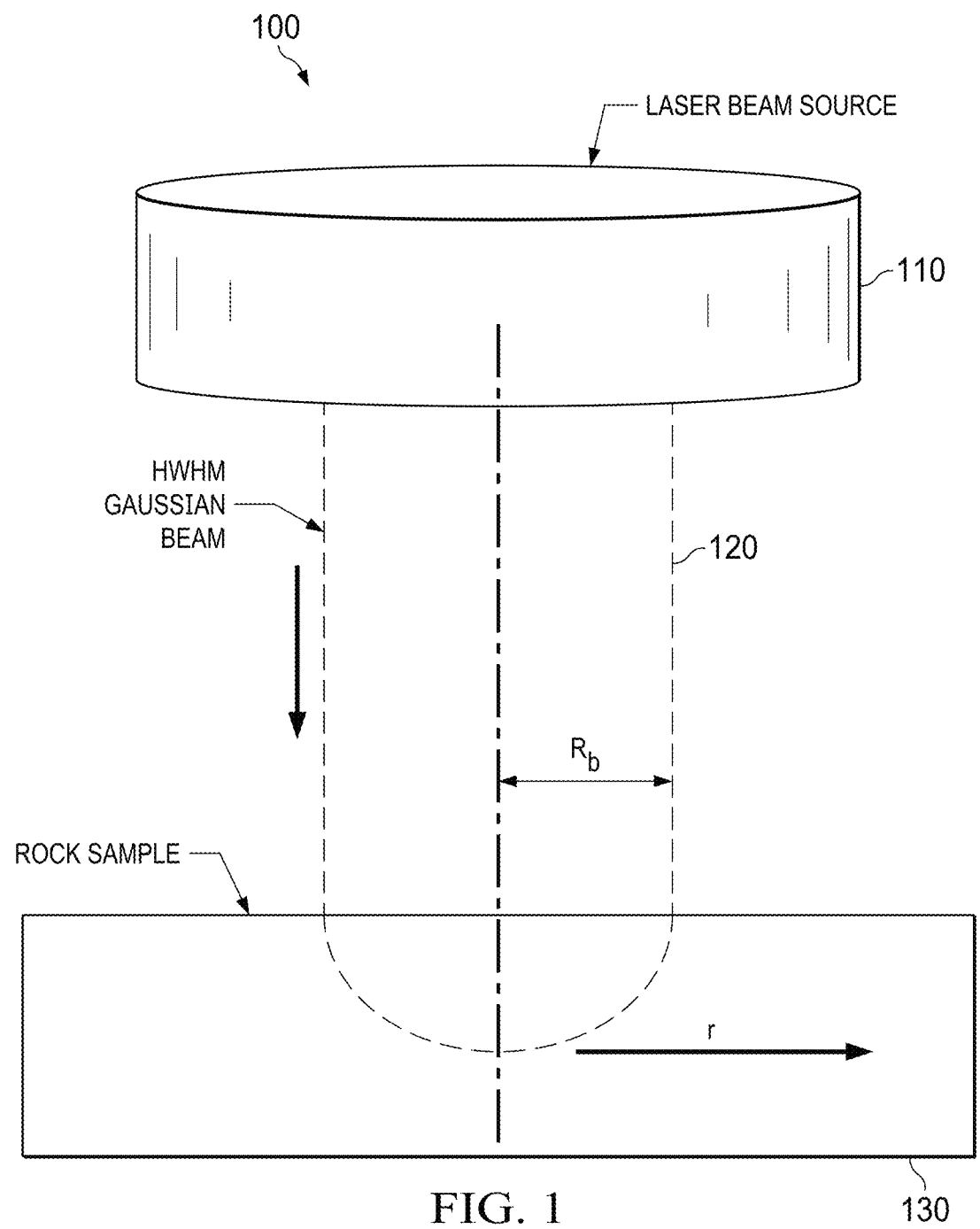
FIG. 1 depicts a schematic graph of a thermal-mechanical interaction model.

FIG. 1 depicts a schematic graph of a thermal-mechanical interaction model 100. The model 100 includes a laser beam source 110, a Gaussian beam 120, and a rock sample 130. Laser beam source 110 is a device that emits light through a process of optical amplification based on the stimulated emission of electromagnetic radiation. The Gaussian beam 120 is emitted from the laser beam source 110, which is given as half widths at half maximum power (HWHM). A Gaussian beam 120 is a beam of monochromatic electromagnetic radiation whose transverse magnetic and electric field amplitude profiles are given by the Gaussian function. The rock sample 130 may be an isotropic or anisotropic sample as well as a homogeneous or heterogeneous sample. The distance away from the central point of the laser beam is labeled as r, and the radius of the Gaussian beam 120 is labeled as $R_b$. The model 100 can be used to simulate the laser beam 120 acting on the surface of the rock sample 130.

Within the described system, the elements of the model 100 can be modeled to simulate the perforating process simulating both the thermal and mechanical elements. In such models, the perforating process is driven by the laser beam 120 front that emits heat on the exposed surface of the rock sample 130. The temperature propagation, thermal expansion, and thermal-mechanical interaction is modeled by coupling heat conduction in solid media with elastic-plastic constitutive mechanical response of rocks. The phase changes occurring in the melting and vaporization processes are accounted for by the latent heats of fusion and vaporization. The heating boundary is updated dynamically during the evolution of perforation channel. The model can be used to predict the penetration rate and mechanical damage as well as the shearing and tensile damage, which may enhance the reservoir's hydraulic conductivity. Parametric study can also be performed using the model to investigate, for example, the effects of material properties; stress ratio; laser beam characteristics on the penetration progress, such as shape and rate; and mechanical damage.

In some implementations, a model and simulations may be implemented using FISH, which is a built-in programming language provided with Fast Lagrangian Analysis of Continua in 3 Dimensions (FLAC3D). FISH can be used as an independent high-level programming language, similar to Fortran and C++. As an embedded programming language in FLAC3D., FISH can access and modify data and computational procedures of FLAC3D models. The simulator used to model the model 100 may be implemented in a template form. In some implementations, the input data and computational subroutines are separate.

Figure 2:
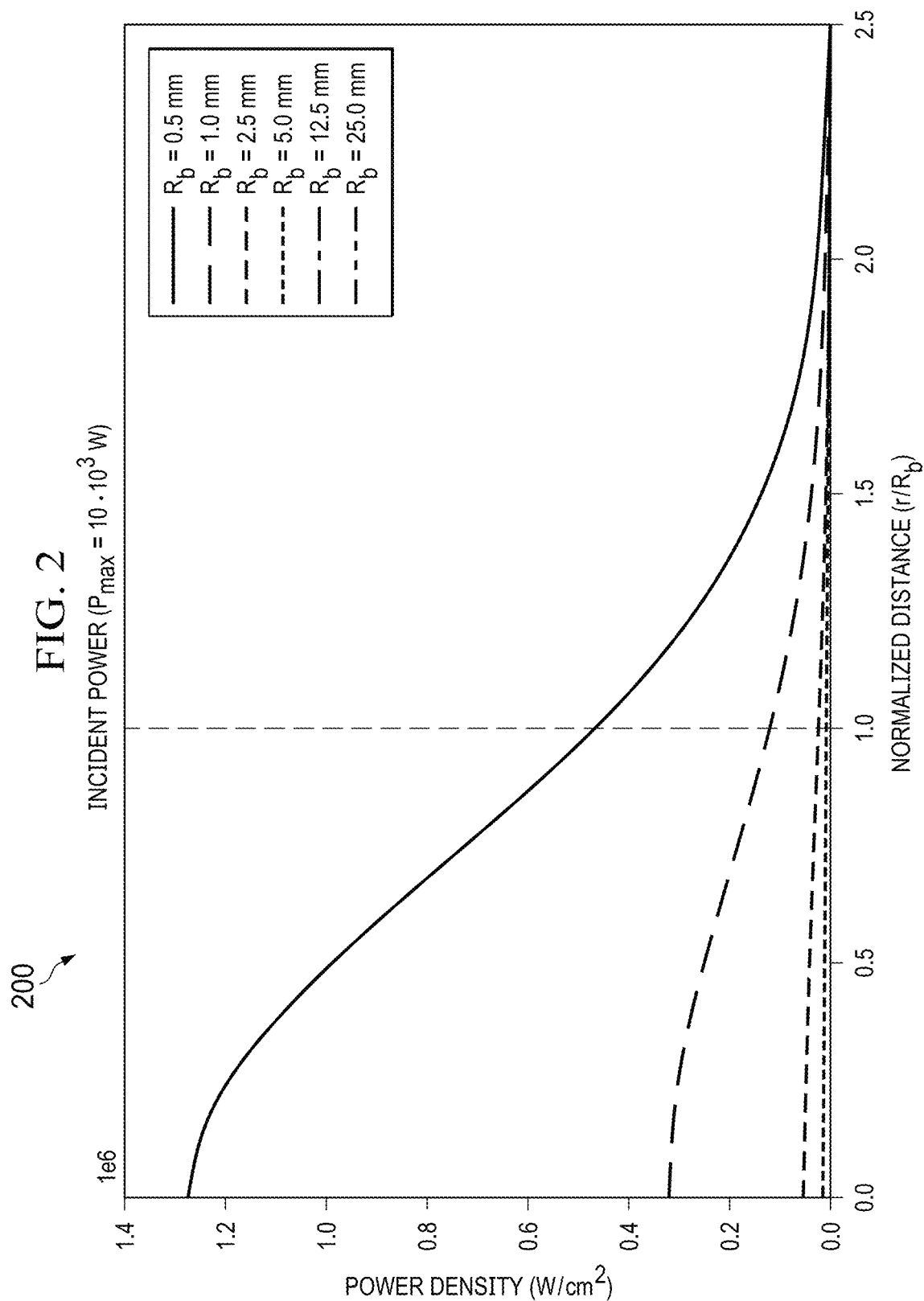
FIG. 2 depicts incident power density as a function of normalized distance.

In some implementations, the laser beam source 110 generates a continuous wave (CW) laser beams that are spatially distributed in a Gaussian-like profile 120. In such examples, the radial intensity distribution is defined as:

$$I_r = I_0 e^{-\frac{2r^2}{R^2}}, \tag{1}$$

where r is the radial distance from the beam center point (see FIG. 1); R is the Gaussian beam radius; and $I_0$ [W/m²] is the on-axis intensity derived from the irradiance-power relation as:

$$I_0 = \frac{2P_t}{\pi R^2}, \tag{2}$$

where $P_t$ [W] is the total power of the Gaussian beam 120. For example, a 5 milliwatt (mW) laser beam, with a waist of 25 millimeters (mm), would yield $I_0$=[W/cm²]. The intensity $I_r$ with various total power values 200 are illustrated in FIG. 2, where at twice the Gaussian radius, the intensity decreases to 0.003% of its peak value and can therefore be neglected.

In some implementations, the heat transfer in dry rock is modeled and the thermal energy is assumed to propagate in the form of thermal conduction which can be described by the transient thermal conduction equation:

$$\rho C_V \frac{\partial T}{\partial t} = \nabla (k\nabla T) + q_V, \tag{3}$$

where ρ [kg/m³] is the density of the rock sample, such as rock sample 130; $C_v$ [J/(kg C)] is the specific heat of a constant volume of the rock sample 130; t[s] is time; T is the temperature [° C.]; k[W/(m ° C.)] is the thermal conductivity of the rock sample; and $q_V$ [W/m³] is the volumetric heat-source intensity. In the modeling of a laser, such as laser source 110, heating of a rock sample, such as rock sample 130, $q_V$ is supplied in the elements on the surface exposed to the radiation of the laser beam, such as Gaussian beam 120.

In some implementations, before running into mechanical plastic yielding state, the rock sample 130 is assumed to behave linear-elastically:

$$\frac{\partial \sigma_{ij}}{\partial t} = 2G\frac{\partial \varepsilon_{ij}}{\partial t} + \left(K - \frac{2}{3}G\right)\frac{\partial C_{kk}}{\partial t}, \tag{4}$$

where $\sigma_{ij}$ [Pa] is the total stress; G[Pa] is the shear modulus of rock sample; $\varepsilon_{ij}$ is the total strain; K[Pa] is the bulk modulus of the rock sample 120.

In some implementations, the plastic mechanical behavior of rock samples, such as rock sample 130, follows an arbitrary failure criterion, such as Mohr-Coulomb failure criterion, with non-associated flow rule in shear yielding but follows associated flow in tensile yielding:

$$f_s = \sigma_1 - \sigma_3 \frac{1 + \sin\phi}{1 - \sin\phi} + 2C_0 \sqrt{\frac{1 + \sin\phi}{1 - \sin\phi}} \tag{5}$$

$$f_t = \sigma_3 - \sigma_t \tag{6}$$

where $f_s$ denotes shear failure criterion; $\sigma_1$ is the maximum principal stress; $\sigma_3$ is the minimum principal stress; Ø is the friction angle; $C_0$ is the cohesive strength; $f_t$ is the tensile failure criterion; $\sigma_t$ is the tensile strength. When $f_s \geq 0$, shear failure occurs; if $f_t \geq 0$, tensile failure occurs.

In some implementations, the mechanical stress is coupled with temperature change via thermal expansion, e.g., in the constitutive relations (Eq. 5) the strain components need to be adjusted to accommodate the thermally induced deformation:

$$\frac{\partial \sigma_{ij}}{\partial t} = 2G\left(\frac{\partial \varepsilon_{ij}}{\partial t} - \alpha_t \frac{\partial T}{\partial t} \delta_{ij}\right) + \left(K - \frac{2}{3}G\right)\left(\frac{\partial \varepsilon_{kk}}{\partial t} - 3\alpha_t \frac{\partial T}{\partial t} \delta_{ij}\right)\sigma_{ij}, \quad (7)$$

where $\alpha_t$ [1/° C.] is the linear thermal expansion coefficient; and $\delta_{ij}$ is the Kronecker Delta.

Figure 3:
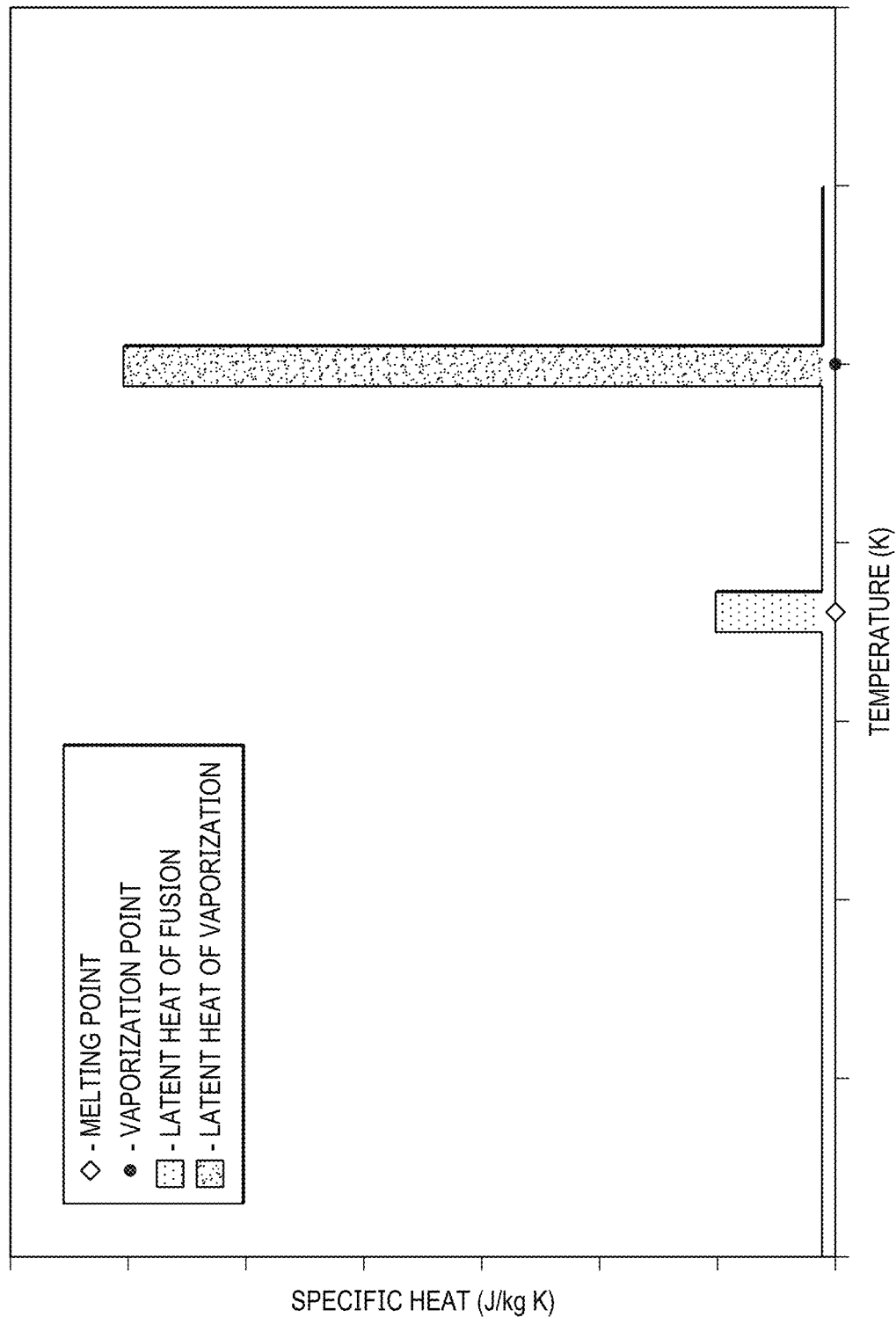
FIG. 3 depicts accommodations of latent heats in the form of temperature dependent specific heat.

In some implementations, due to laser beam heating, a thin layer of material on the exposed surface melts by absorption of laser energy. After some time, the surface of this layer vaporizes after it reaches the vaporization temperature. In the sudden expansion of vapor, some material may resolidify when it is pushed out of the melt pool. Besides two phase changes, e.g., melting and vaporization, the laser heating process also involves free surface flow of the melting material, multiphase heat transfer via conduction and convection, dynamics of vaporized gas, resolidification, and so forth. In the described system, the latent heats are considered in the form of time-dependent specific heat, e.g., the specific heat is adjusted around the melting point and vaporization point across a temperature range such that latent heat will be absorbed over this range, as illustrated in FIG. 3, where accommodations of latent heats in the form of temperature dependent specific heat 300 are depicted.

Figure 4:
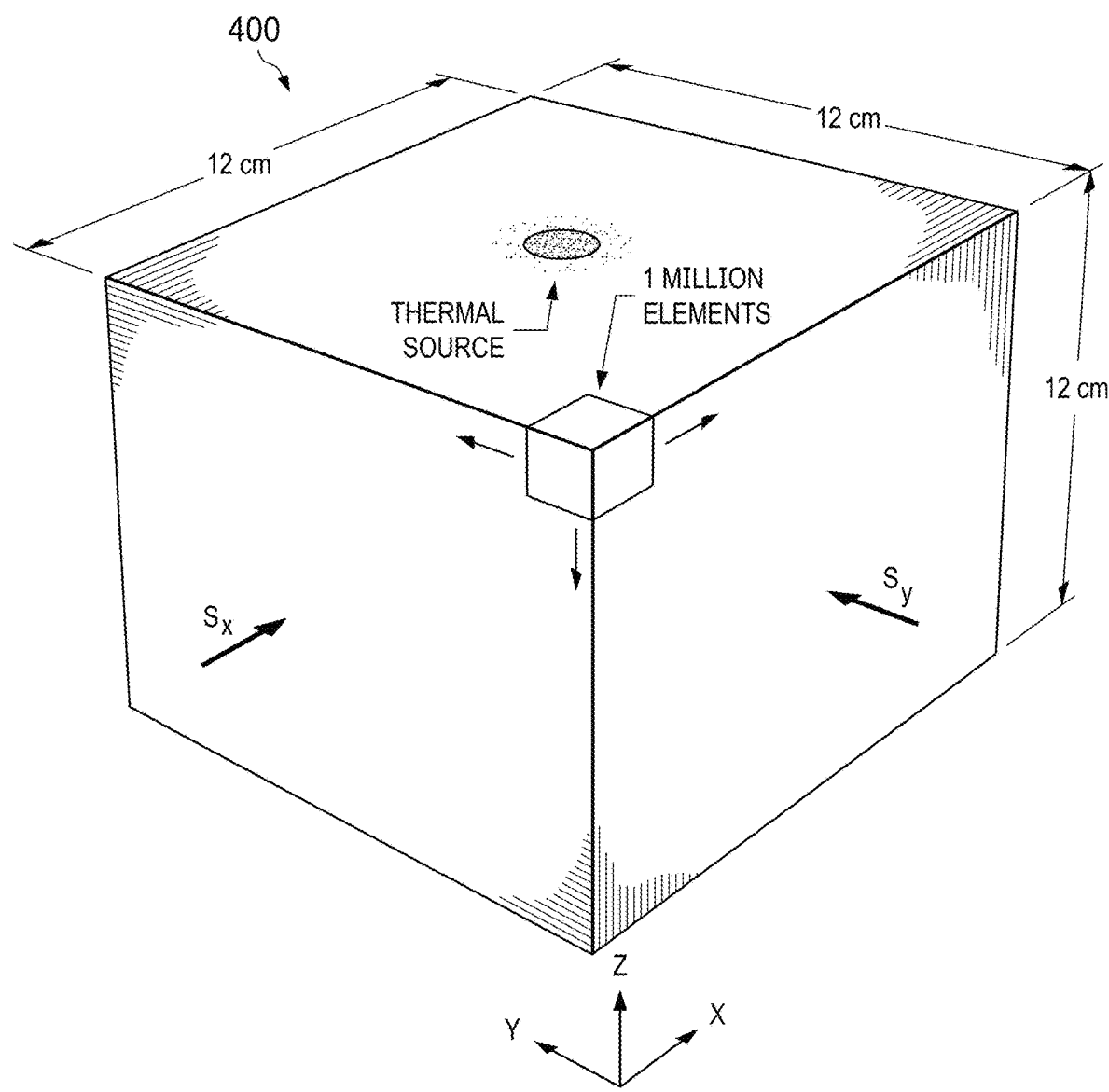
FIG. 4 depicts a block model that shows a potential numerical discretization for modeling rock sample.
Figure 5B:
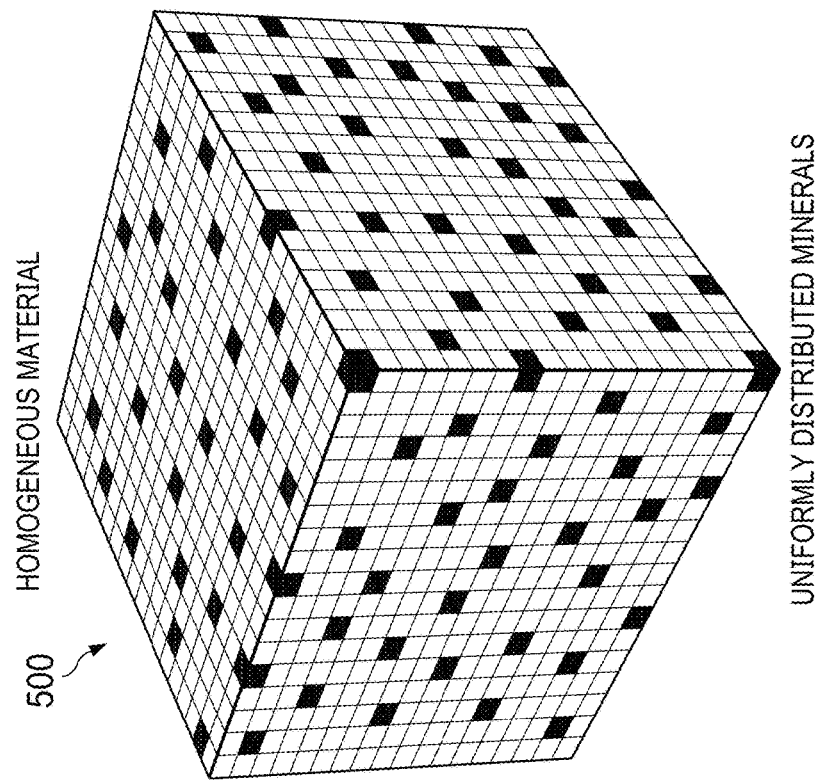
FIGS. 5A-5D depict homogeneous and heterogeneous materials that comprise a rock sample.
Figure 5A:
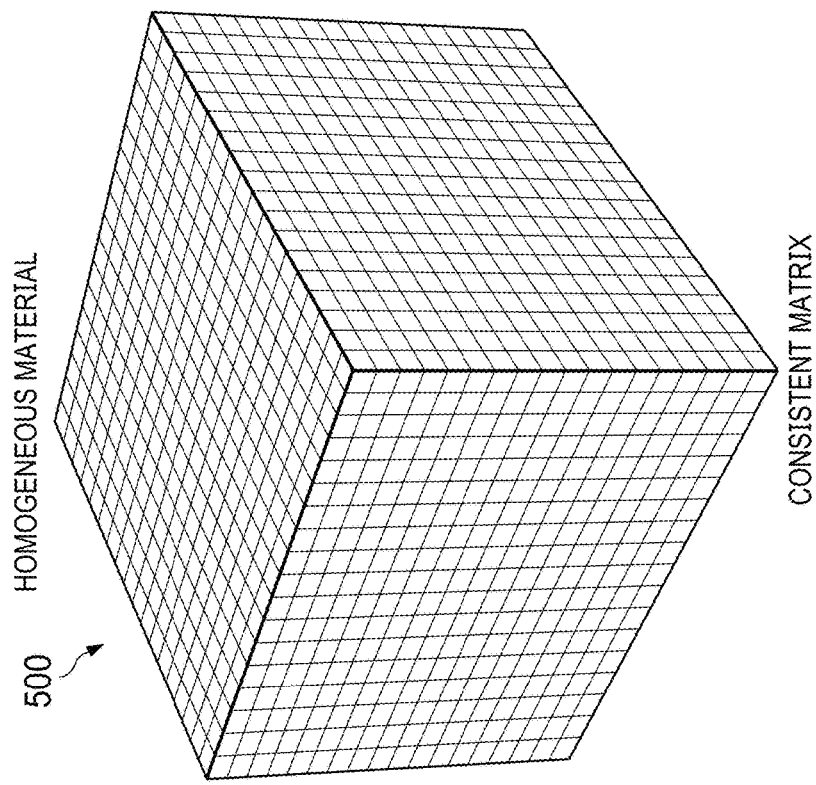
Figure 5D:
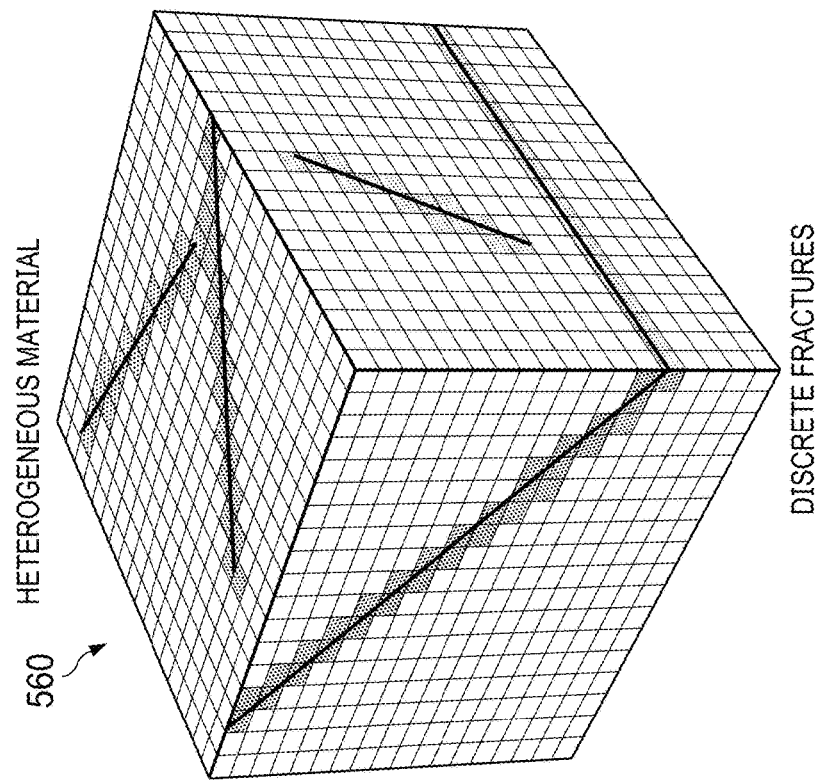
Figure 5C:
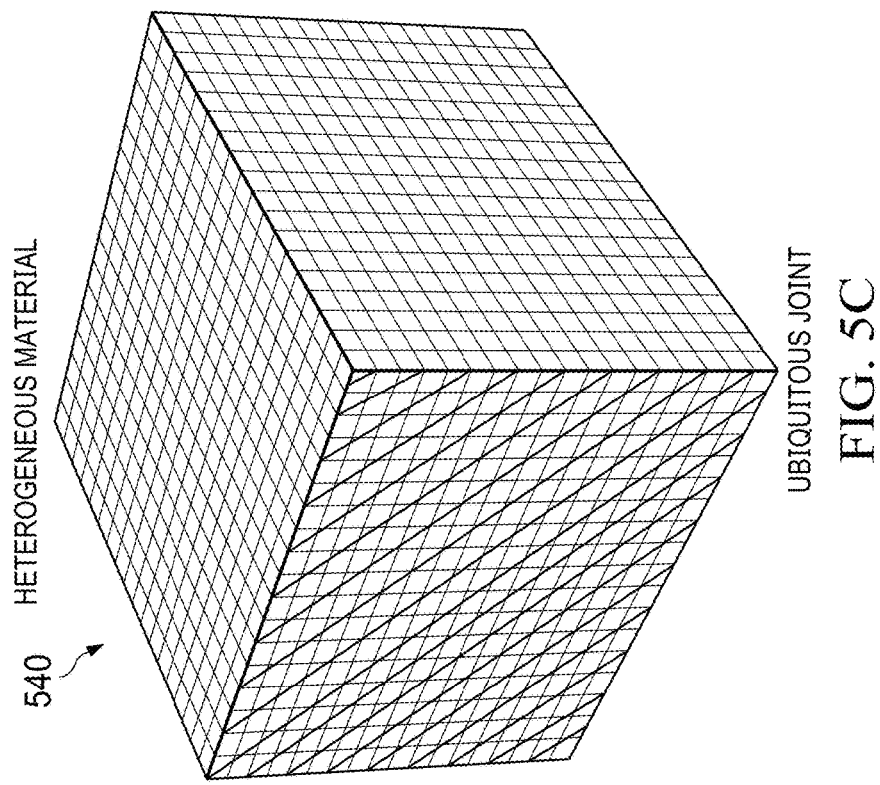

The anisotropy of the rocks is reflected in their mechanical, hydraulic, and thermal properties. For example, the elastic response of a layered rock in which the elastic moduli are significantly different in directions perpendicular and parallel to the layers can be modeled by the transversely isotropic model. If the strength of weak planes embedded in the rock is different from the rock matrix, the plastic behavior of the rock may be described by the ubiquitous-joint model. Similarly, the layered rocks also have different thermal properties (e.g., conductivity) and hydraulic properties (e.g., permeability) in different directions, which can be modeled by the anisotropic thermal model and fluid model. FIG. 4 depicts a block 400 model. As depicted, the left side of the block model 400 shows a potential numerical discretization for modeling a $12^3$ cm³ rock sample, which could be isotropic homogeneous with consistent material properties for all the elements as depicted in FIG. 5A, anisotropic but homogeneous (e.g., heterogeneous minerals that are homogeneously/randomly distributed) as depicted in FIG. 5B, isotropic but heterogeneous with ubiquitous joints as depicted in FIG. 5C, or contain discrete fractures orientated with specific ranges as depicted in FIG. 5D. Since each element in a model in the described system can be assigned a different constitutive model, or same constitutive model but with different mechanical properties, the heterogeneities can be accommodated naturally in the developed simulator.

Figure 6A:
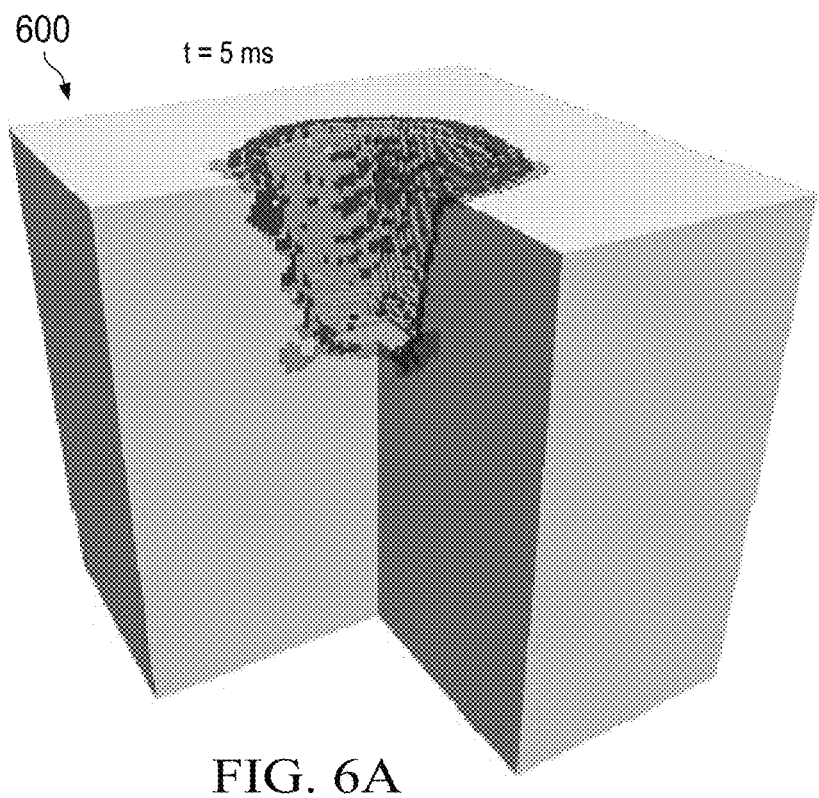
FIGS. 6A-6D, 7A-7D, and 8A-8D depict example results from modeling of laser-perforation on rock samples that measure the impact of various bedding cohesive strength for certain time intervals.
Figure 6B:
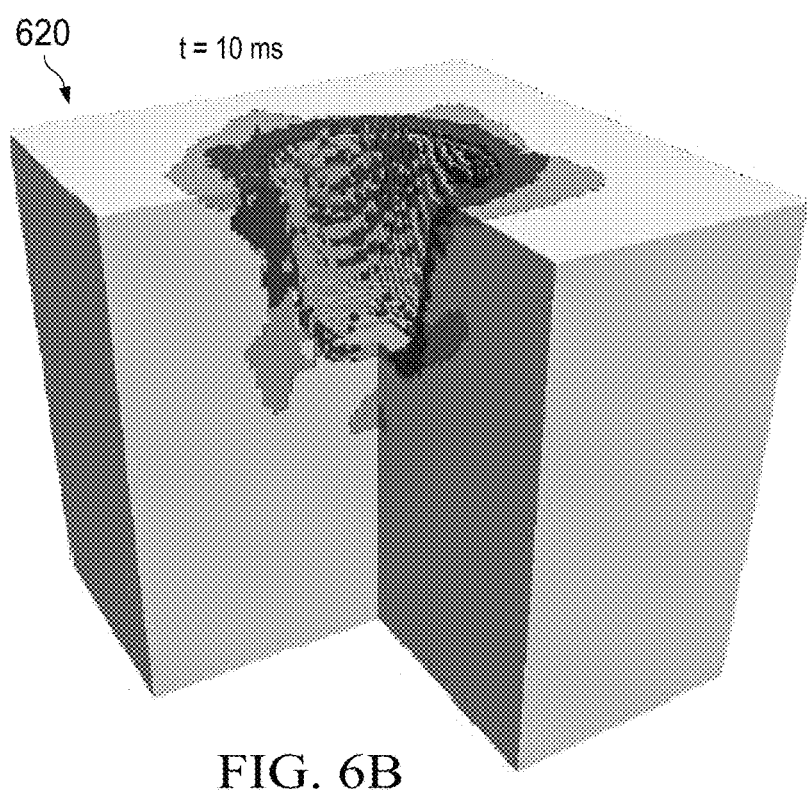
Figure 6C:
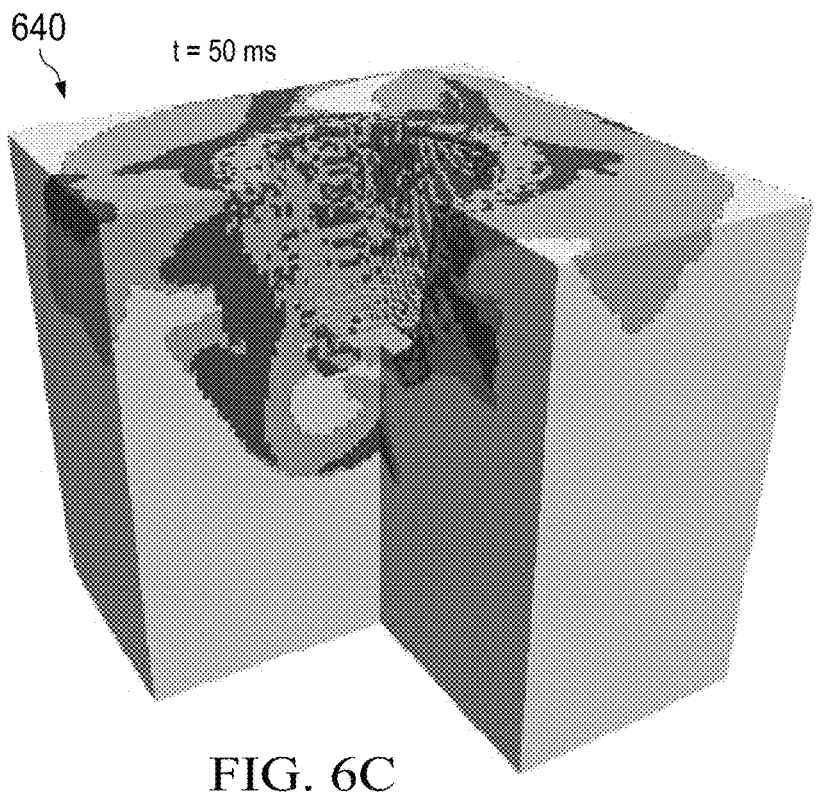
Figure 6D:
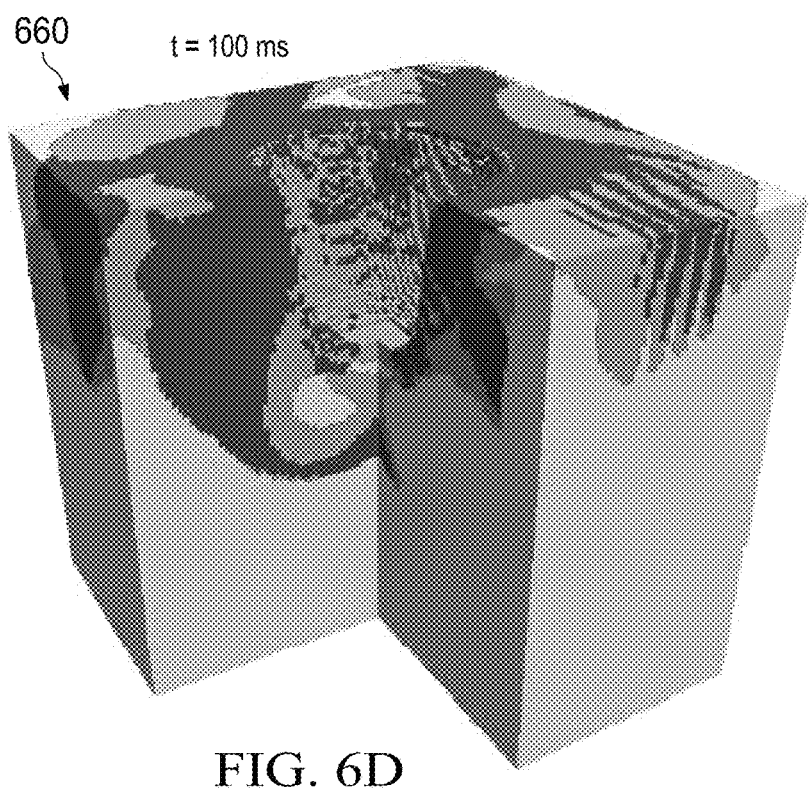
Figure 7A:
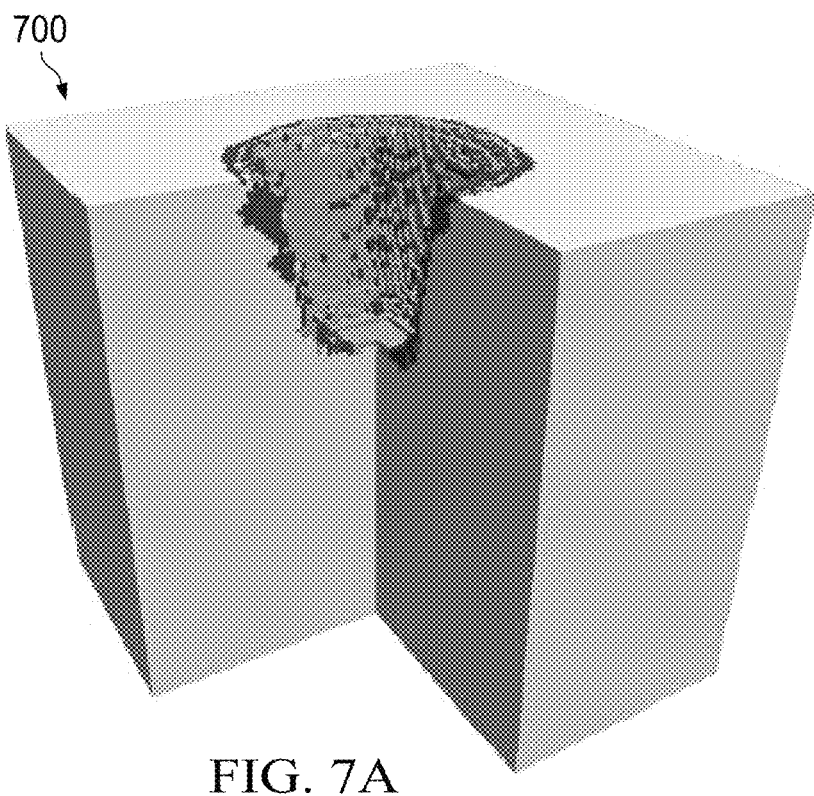
Figure 7B:
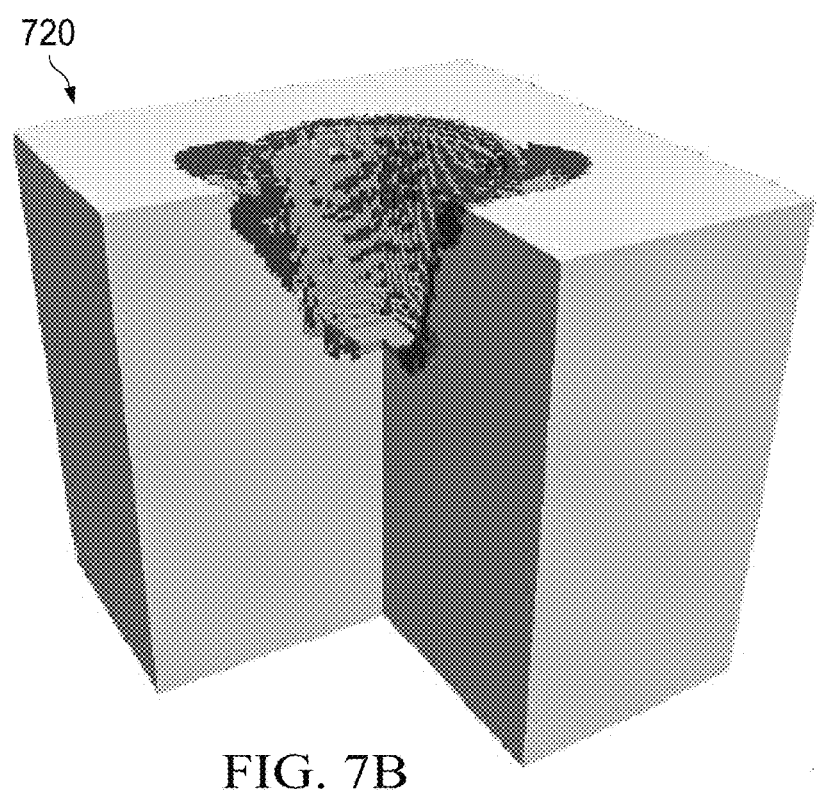
Figure 7C:
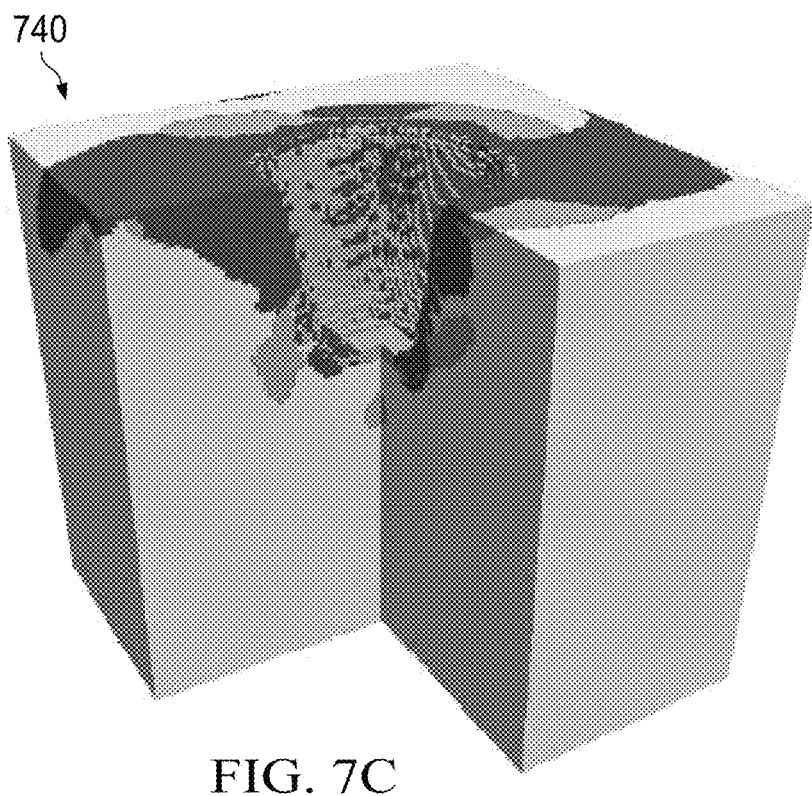
Figure 7D:
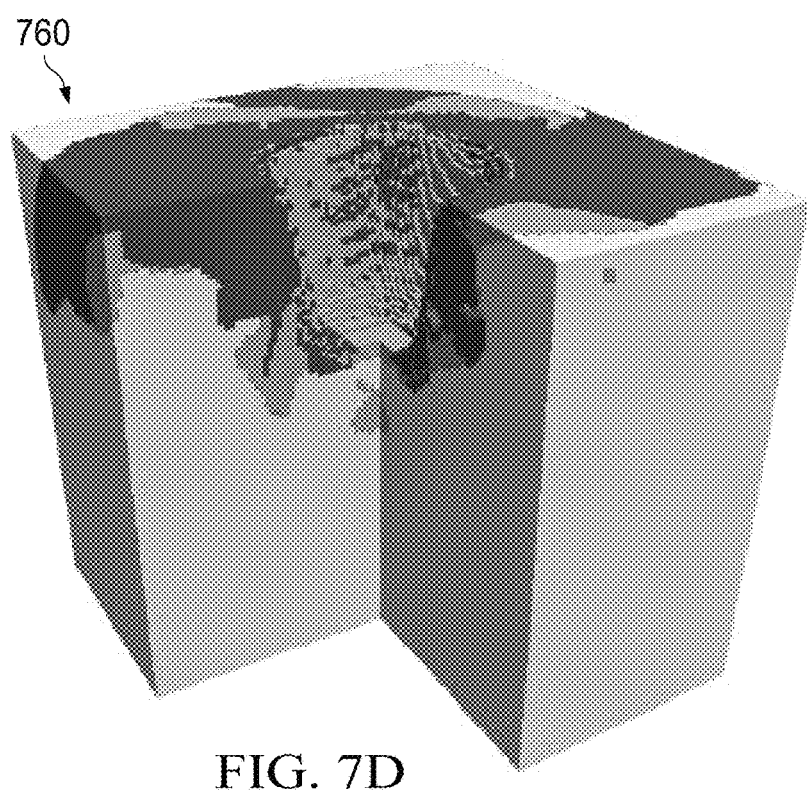
Figure 8A:
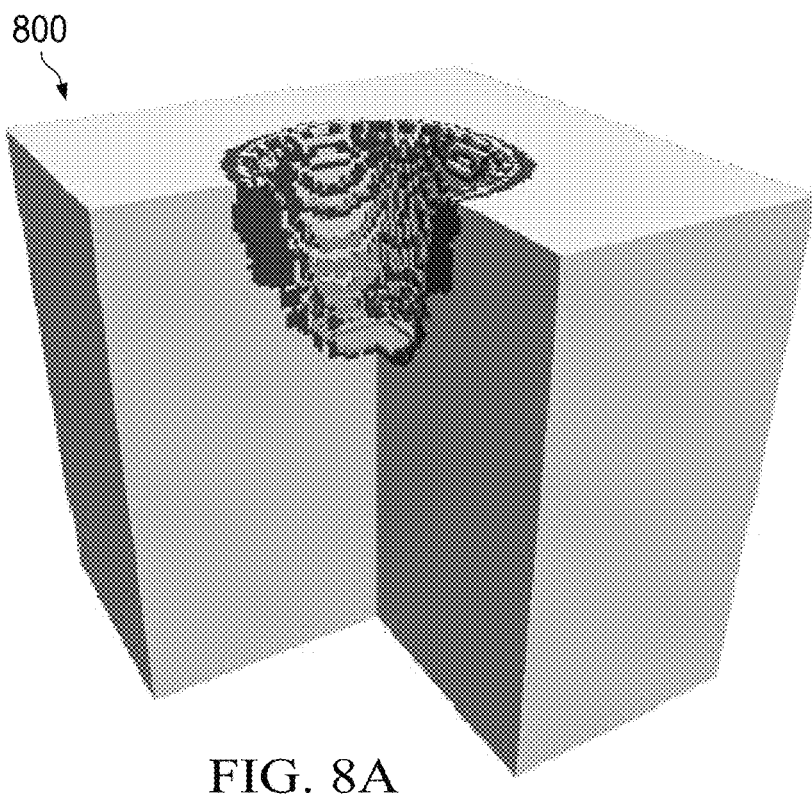
Figure 8B:
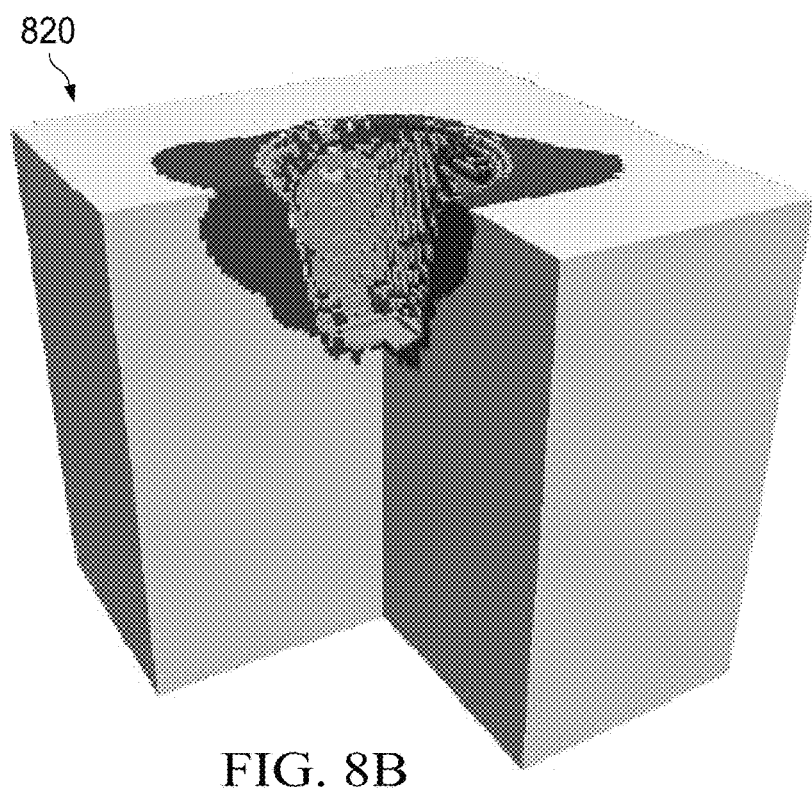
Figure 8C:
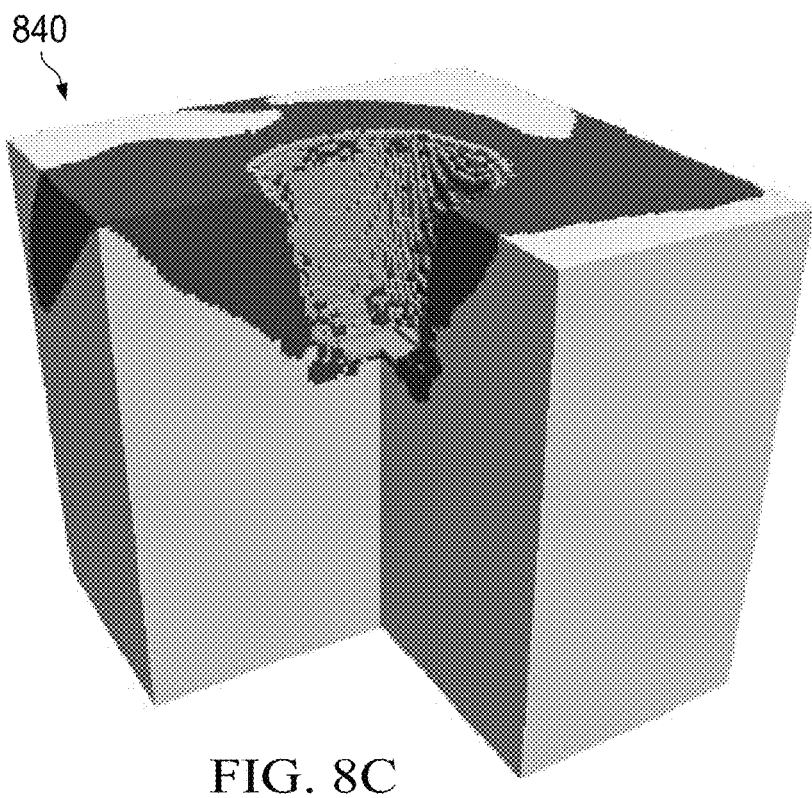
Figure 8D:
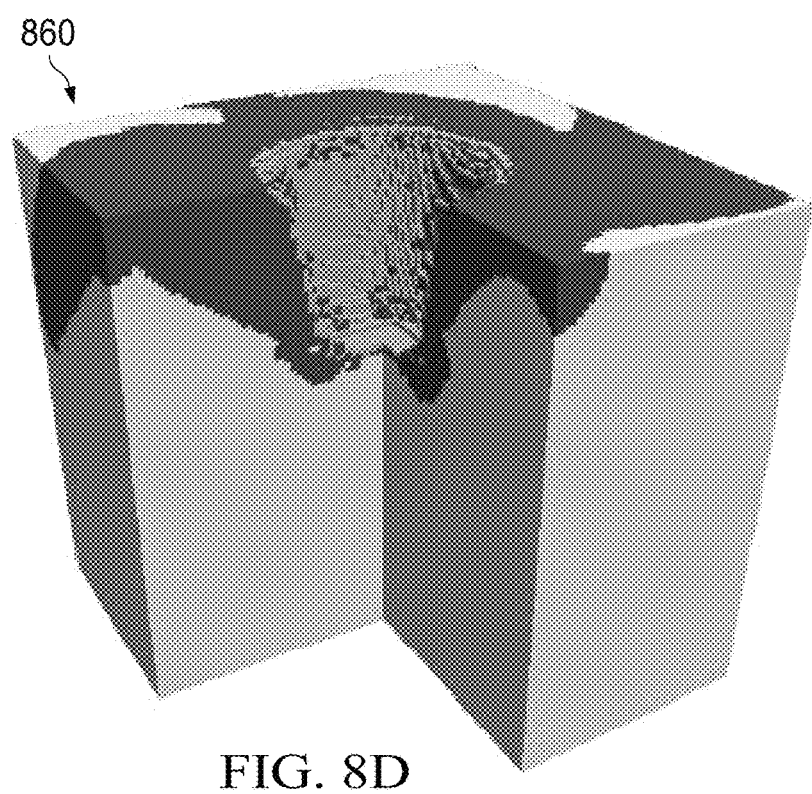

FIGS. 6A-6D, 7A-7D, and 8A-8D depict how bedding cohesive strength affects the mechanical damage around the perforation channel generated by laser with various heating times. FIGS. 6A-6D depict the impact with a bedding cohesive strength=5% of matrix cohesive strength. FIGS. 7A-7D depict the impact with a bedding cohesive strength=10% of matrix cohesive strength. FIGS. 8A-8D depict the impact with a bedding cohesive strength=50% of matrix cohesive strength. The depicted simulation assumes that the rock sample contains uniformly distributed bedding planes with an arbitrary dip direction, such as 45°, and an arbitrary dip angle, such as 60°. The rock matrix has thermal and mechanical properties as shown in Table 1 below. The cohesive strength, frictional angle, and tensile strength on the weak planes may be lower than those of rock matrix. FIGS. 6A, 7A, and 8A depict the perforation channel generated by laser heating at a time of 5 milliseconds (ms). FIGS. 6B, 7B, and 8B depict the perforation channel generated by laser heating at a time of 10 ms. FIGS. 6C, 7C, and 8C depict the perforation channel generated by laser heating at a time of 50 ms. FIGS. 6D, 7D, and 8D depict the perforation channel generated by laser heating at a time of 100 ms.

As can be seen, for the weaker beddings, e.g., bedding cohesive strength is 10% or 5% of matrix cohesive strength, both shearing and tensile yielding regions increase with time. For stronger bedding (e.g., bedding cohesive strength is 50% of matrix cohesive strength) the tensile yield dominates the mechanical damage response. In all three cases, tensile yielding regions are similar at all times because bedding tensile strength is set identical to the matrix tensile strength. At large times, the shear yielding region increases as the bedding cohesive strength decreases.

TABLE 1

Mechanical and Thermal Properties of Rock Sample

| Property | Value |
|---|---|
| Density ($\rho$, kg/m³) | 2250 |
| Shear Modulus (G, Pa) | 39.7e9 |
| Bulk Modulus (K, Pa) | 69.4e9 |
| Poisson's Ratio (v) | 0.26 |
| Cohesive Strength ($C_0$, Pa) | 26.0e6 |
| Friction Angle ($\phi$, deg) | 26.4 |
| Dilation Angle ($\psi$, deg) | 6.6 |
| Tensile Strength ($\sigma^T$, Pa) | 2.1e6 |
| Thermal Conductivity ($\kappa$, w/m k) | 2.5 |
| Specific Heat ($C_v$, J/kg k) | 920.0 |
| Thermal Expansion Coeff. ($\alpha_t$, /F) | 1.16e−5 |
| Melting Point ($T_m$, F) | 1813 |
| Latent Heat of Fusion (J/kg) | 2.0e6 |
| Vaporization Point ($T_f$, F) | 2470 |
| Latent Heat of Vaporization (J/kg) | 13.3e6 |

Figure 9:
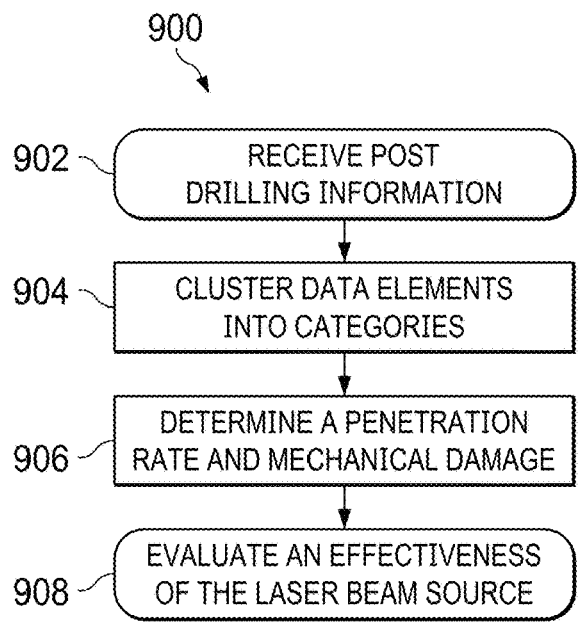
FIG. 9 depicts a flow diagram of an example process for evaluating an effectiveness of the laser beam source to be used in a perforation at the drilling site based on the determined penetration rate and mechanical damage.

FIG. 9 depicts a flow diagram of an example process (900) for evaluating an effectiveness of the laser beam source to be used in a perforation at the drilling site based on the determined penetration rate and mechanical damage. For clarity of presentation, the description that follows generally describes method 900 in the context of FIGS. 1-8D and 10. However, it will be understood that method 900 may be performed, for example, by any other suitable system, environment, software, and hardware, or a combination of systems, environments, software, and hardware as appropriate. In some implementations, various steps of method 900 can be run in parallel, in combination, in loops, or in any order.

The process receives (902) a rock sample data regarding a rock sample from a drilling site. A thermal-mechanical interaction model is generated (904) based on the rock sample data. A penetration rate and mechanical damage around perforation channels is determined (906) from the thermal-mechanical interaction model through modeling of heat emitted on an exposed surface of a rock sample by a laser beam emitted from a laser beam source. An effectiveness of the laser beam source to be used in a perforation at the drilling site is evaluated (908) based on the determined penetration rate and mechanical damage and the process 900 ends.

Figure 10:
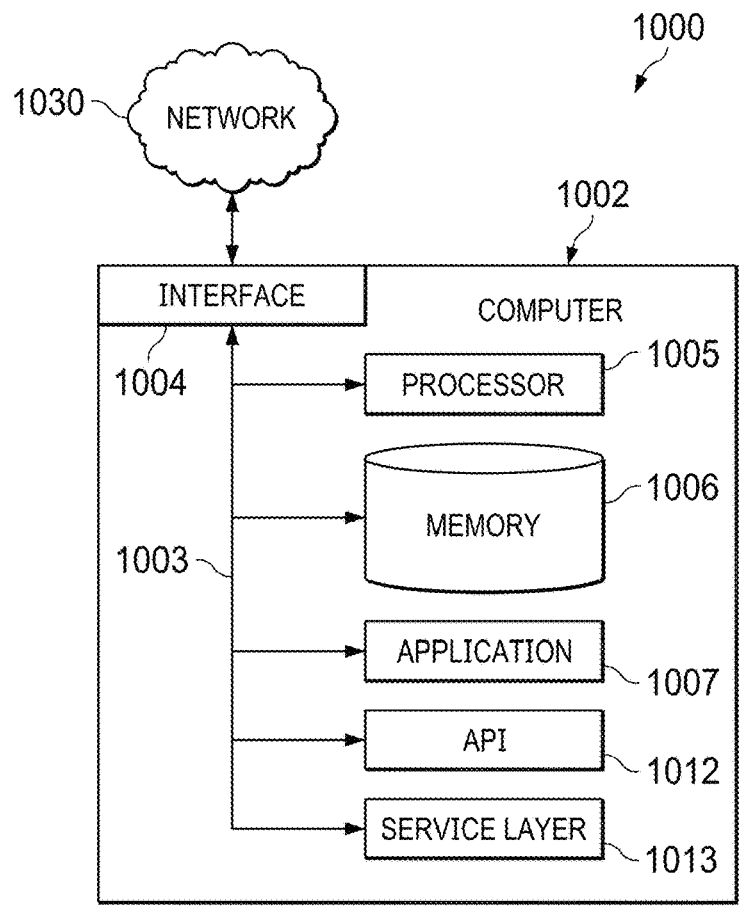
FIG. 10 illustrates a block diagram of an exemplary computer system used to provide computational functionalities associated with described algorithms, methods, functions, processes, flows, and procedures as described in the instant disclosure, according to an implementation.

FIG. 10 depicts a block diagram of an exemplary computer system 1000 used to provide computational functionalities associated with described algorithms, methods, functions, processes, flows, and procedures as described in the instant disclosure, according to an implementation. The illustrated computer 1002 is intended to encompass any computing device such as a server, desktop computer, laptop or notebook computer, wireless data port, smart phone, personal data assistant (PDA), tablet computing device, one or more processors within these devices, or any other suitable processing device, including both physical or virtual instances (or both) of the computing device. Additionally, the computer 1002 may comprise a computer that includes an input device, such as a keypad, keyboard, touch screen, or other device that can accept user information, and an output device that conveys information associated with the operation of the computer 1002, including digital data, visual, or audio information (or a combination of information), or a GUI.

The computer 1002 can serve in a role as a client, network component, a server, a database or other persistency, or any other component (or a combination of roles) of a computer system for performing the subject matter described in the instant disclosure. The illustrated computer 1002 is communicably coupled with a network 1030. In some implementations, one or more components of the computer 1002 may be configured to operate within environments, including cloud-computing-based, local, global, or other environment (or a combination of environments).

At a high level, the computer 1002 is an electronic computing device operable to receive, transmit, process, store, or manage data and information associated with the described subject matter. According to some implementations, the computer 1002 may also include or be communicably coupled with an application server, e-mail server, web server, caching server, streaming data server, business intelligence (BI) server, or other server (or a combination of servers).

The computer 1002 can receive requests over network 1030 from a client application (for example, executing on another computer 1002) and responding to the received requests by processing the said requests in an appropriate software application. In addition, requests may also be sent to the computer 1002 from internal users (for example, from a command console or by other appropriate access method), external or third-parties, other automated applications, as well as any other appropriate entities, individuals, systems, or computers.

Each of the components of the computer 1002 can communicate using a system bus 1003. In some implementations, any or all of the components of the computer 1002, both hardware or software (or a combination of hardware and software), may interface with each other or the interface 1004 (or a combination of both) over the system bus 1003 using an application programming interface (API) 1012 or a service layer 1013 (or a combination of the API 1012 and service layer 1013). The API 1012 may include specifications for routines, data structures, and object classes. The API 1012 may be either computer-language independent or dependent and refer to a complete interface, a single function, or even a set of APIs. The service layer 1013 provides software services to the computer 1002 or other components (whether or not illustrated) that are communicably coupled to the computer 1002. The functionality of the computer 1002 may be accessible for all service consumers using this service layer. Software services, such as those provided by the service layer 1013, provide reusable, defined business functionalities through a defined interface. For example, the interface may be software written in JAVA, C++, or other suitable language providing data in extensible markup language (XML) format or other suitable format. While illustrated as an integrated component of the computer 1002, alternative implementations may illustrate the API 1012 or the service layer 1013 as stand-alone components in relation to other components of the computer 1002 or other components (whether or not illustrated) that are communicably coupled to the computer 1002. Moreover, any or all parts of the API 1012 or the service layer 1013 may be implemented as child or sub-modules of another software module, enterprise application, or hardware module without departing from the scope of this disclosure.

The computer 1002 includes an interface 1004. Although illustrated as a single interface 1004 in FIG. 10, two or more interfaces 1004 may be used according to particular needs, desires, or particular implementations of the computer 1002. The interface 1004 is used by the computer 1002 for communicating with other systems in a distributed environment that are connected to the network 1030 (whether illustrated or not). Generally, the interface 1004 comprises logic encoded in software or hardware (or a combination of software and hardware) and operable to communicate with the network 1030. More specifically, the interface 1004 may comprise software supporting one or more communication protocols associated with communications such that the network 1030 or interface's hardware is operable to communicate physical signals within and outside of the illustrated computer 1002.

The computer 1002 includes a processor 1005. Although illustrated as a single processor 1005 in FIG. 10, two or more processors may be used according to particular needs, desires, or particular implementations of the computer 1002. Generally, the processor 1005 executes instructions and manipulates data to perform the operations of the computer 1002 and any algorithms, methods, functions, processes, flows, and procedures as described in the instant disclosure.

The computer 1002 also includes a memory 1006 that holds data for the computer 1002 or other components (or a combination of both) that can be connected to the network 1030 (whether illustrated or not). For example, memory 1006 can be a database storing data consistent with this disclosure. Although illustrated as a single memory 1006 in FIG. 10, two or more memories may be used according to particular needs, desires, or particular implementations of the computer 1002 and the described functionality. While memory 1006 is illustrated as an integral component of the computer 1002, in alternative implementations, memory 1006 can be external to the computer 1002.

The application 1007 is an algorithmic software engine providing functionality according to particular needs, desires, or particular implementations of the computer 1002, particularly with respect to functionality described in this disclosure. For example, application 1007 can serve as one or more components, modules, applications, etc. Further, although illustrated as a single application 1007, the application 1007 may be implemented as multiple applications 1007 on the computer 1002. In addition, although illustrated as integral to the computer 1002, in alternative implementations, the application 1007 can be external to the computer 1002.

There may be any number of computers 1002 associated with, or external to, a computer system containing computer 1002, each computer 1002 communicating over network 1030. Further, the term "client," "user," and other appropriate terminology may be used interchangeably as appropriate without departing from the scope of this disclosure. Moreover, this disclosure contemplates that many users may use one computer 1002, or that one user may use multiple computers 1002.

Described implementations of the subject matter can include one or more features, alone or in combination. For example, in a first implementation, a computer-implemented method executed by one or more processors, the method comprising: receiving rock sample data regarding a rock sample from a drilling site; generating a thermal-mechanical interaction model based on the rock sample data; determining, from the thermal-mechanical interaction model, a penetration rate and mechanical damage around perforation channels through modeling of heat emitted on an exposed surface of a rock sample by a laser beam emitted from a laser beam source; and evaluating an effectiveness of the laser beam source to be used in a perforation at the drilling site based on the determined penetration rate and mechanical damage.

The foregoing and other described implementations can each optionally include one or more of the following features.

A first feature, combinable with any of the following features, wherein the mechanical damage includes deformation and damage processes inside rock sample.

A second feature, combinable with any of the previous or following features, wherein the rock sample include uniformly distributed bedding planes with arbitrary dip direction and dip angle.

A third feature, combinable with any of the previous or following features, wherein the rock sample is isotropic or anisotropic.

A fourth feature, combinable with any of the previous or following features, wherein the rock sample is homogeneous or heterogeneous.

A fifth feature, combinable with any of the previous or following features, wherein the laser beam is a Gaussian beam.

A sixth feature, combinable with any of the previous or following features, comprising determining temperature propagation, thermal expansion, and thermal-mechanical interaction through the modeling of the heat emitted on the exposed surface of the rock sample by the laser beam.

A seventh feature, combinable with any of the previous or following features, wherein a heating boundary is updated dynamically during an evolution of the perforation channels within the thermal-mechanical interaction model.

An eighth feature, combinable with any of the previous or following features, wherein phase changes occurring in a melting and vaporization process are accounted for by latent heats of fusion and vaporization within the thermal-mechanical interaction model.

A ninth feature, combinable with any of the previous or following features, wherein the thermal-mechanical interaction model simulates a heat transfer in the rock sample, and wherein thermal energy propagate in a form of thermal conduction that is described in the thermal-mechanical interaction model according to a transient thermal conduction equation.

A tenth feature, combinable with any of the previous or following features, wherein the transient thermal conduction equation is described according to:

$$\rho C_V \frac{\partial T}{\partial t} = \nabla(k \nabla T) + q_V,$$

wherein $\rho$ [kg/m$^3$] is a density of the rock sample; $C_v$ [J/(kg C)] is a specific heat of a constant volume of the rock sample; t[s] is a time; T is a temperature [° C.]; k[W/(m ° C.)] is a thermal conductivity of the rock sample; and $q_V$ [W/m$^3$] is a volumetric heat-source intensity.

An eleventh feature, combinable with any of the previous or following features, wherein a plastic mechanical behavior of the rock sample follows an arbitrary failure criterion that has a non-associated flow rule in shear yielding and follows an associated flow in tensile yielding according to:

$$f_s = \sigma_1 - \sigma_3 \frac{1+\sin\phi}{1-\sin\phi} + 2C_0 \sqrt{\frac{1+\sin\phi}{1-\sin\phi}} \text{ and } f_t = \sigma_3 - \sigma_t,$$

wherein $f_s$ denotes a shear failure criterion; $\sigma_1$ is a maximum principal stress; $\sigma_3$ is a minimum principal stress; Ø is a friction angle; $C_0$ is a cohesive strength; $f_t$ is a tensile failure criterion; $\sigma_t$ is a tensile strength.

In a second implementation, one or more non-transitory computer-readable storage media coupled to one or more processors have instructions stored thereon which, when executed by the one or more processors, cause the one or more processors to perform operations comprising: receiving rock sample data regarding a rock sample from a drilling site; generating a thermal-mechanical interaction model based on the rock sample data; determining, from the thermal-mechanical interaction model, a penetration rate and mechanical damage around perforation channels through modeling of heat emitted on an exposed surface of a rock sample by a laser beam emitted from a laser beam source; and evaluating an effectiveness of the laser beam source to be used in a perforation at the drilling site based on the determined penetration rate and mechanical damage.

The foregoing and other described implementations can each optionally include one or more of the following features.

A first feature, combinable with any of the following features, wherein the mechanical damage includes deformation and damage processes inside rock sample.

A second feature, combinable with any of the previous or following features, wherein the rock sample include uniformly distributed bedding planes with arbitrary dip direction and dip angle.

A third feature, combinable with any of the previous or following features, wherein the operations further comprise: determining temperature propagation, thermal expansion, and thermal-mechanical interaction through the modeling of the heat emitted on the exposed surface of the rock sample by the laser beam.

In a third implementation, a computer-implemented system, comprises: one or more processors; and a computer-readable storage device coupled to the one or more processors and having instructions stored thereon which, when executed by the one or more processors, cause the one or more processors to perform operations comprising: receiving rock sample data regarding a rock sample from a drilling site; generating a thermal-mechanical interaction model based on the rock sample data; determining, from the thermal-mechanical interaction model, a penetration rate and mechanical damage around perforation channels through modeling of heat emitted on an exposed surface of a rock sample by a laser beam emitted from a laser beam source; and evaluating an effectiveness of the laser beam source to be used in a perforation at the drilling site based on the determined penetration rate and mechanical damage.

A first feature, combinable with any of the following features, wherein a heating boundary is updated dynamically during an evolution of the perforation channels within the thermal-mechanical interaction model.

A second feature, combinable with any of the previous or following features, wherein phase changes occurring in a melting and vaporization process are accounted for by latent heats of fusion and vaporization within the thermal-mechanical interaction model.

A third feature, combinable with any of the previous or following features, wherein the thermal-mechanical interaction model simulates a heat transfer in the rock sample, and wherein thermal energy propagate in a form of thermal conduction that is described in the thermal-mechanical interaction model according to a transient thermal conduction equation.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, that is, one or more modules of computer program instructions encoded on a tangible, non-transitory, computer-readable computer-storage medium for execution by, or to control the operation of, data processing apparatus. Alternatively or in addition, the program instructions can be encoded on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) may be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, IOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with this disclosure), all or a portion of the Internet, or any other communication system or systems at one or more locations (or a combination of communication networks). The network may communicate with, for example, Internet Protocol (IP) packets, Frame Relay frames, Asynchronous Transfer Mode (ATM) cells, voice, video, data, or other suitable information (or a combination of communication types) between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware or software (or a combination of hardware and software), may interface with each other or the interface using an application programming interface (API) or a service layer (or a combination of API and service layer). The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers using this service layer. Software services provide reusable, defined business functionalities through a defined interface. For example, the interface may be software written in JAVA, C++, FISH, or other suitable language providing data in extensible markup language (XML) format or other suitable format. The API or service layer (or a combination of the API and the service layer) may be an integral or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described earlier as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the implementations described earlier should not be understood as requiring such separation or integration in all implementations, and it should be understood that the described program components and systems can generally be integrated together in a single software product or packaged into multiple software products.

Accordingly, the earlier description of example implementations does not define or constrain this disclosure.

Other changes, substitutions, and alterations are also possible without departing from the spirit and scope of this disclosure.

Furthermore, any claimed implementation described later is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

The invention claimed is:

1. A computer-implemented method executed by one or more processors, the method comprising:
   receiving rock sample data regarding a rock sample from a drilling site; generating a thermal-mechanical interaction model based on the rock sample data, wherein the thermal-mechanical interaction model simulates heat transfer in the rock sample, wherein thermal energy propagates in a form of thermal conduction that is described in the thermal-mechanical interaction model according to a transient thermal conduction equation, and wherein the transient thermal conduction equation is described according to:

$$\rho C_V \frac{\partial T}{\partial t} = \nabla(k\nabla T) + q_V,$$

wherein:
   $\rho$ [kg/m$^3$] is the density of the rock sample; $C_v$ [J/(kg C)] is the specific heat of a constant volume of the rock sample; t[s] is time; T is the temperature [° C.]; k[W/(m ° C.)] is a thermal conductivity of the rock sample; and $q_V$ [W/m$^3$] is a volumetric heat-source intensity;
   determining, from the thermal-mechanical interaction model, a penetration rate and mechanical damage around perforation channels through modeling of heat emitted on an exposed surface of the rock sample by a laser beam emitted from a laser beam source; and
   evaluating an effectiveness of the laser beam source to be used in a perforation at the drilling site based on the determined penetration rate and mechanical damage.

2. The method of claim 1, wherein the mechanical damage includes deformation and damage processes inside the rock sample.

3. The method of claim 1, wherein the rock sample include uniformly distributed bedding planes with arbitrary dip direction and dip angle.

4. The method of claim 1, wherein the rock sample is isotropic or anisotropic.

5. The method of claim 1, wherein the rock sample is homogeneous or heterogeneous.

6. The method of claim 1, wherein the laser beam is a Gaussian beam.

7. The method of claim 1, further comprising:
   determining temperature propagation, thermal expansion, and thermal-mechanical interaction through the modeling of the heat emitted on the exposed surface of the rock sample by the laser beam.

8. The method of claim 1, wherein a heating boundary is updated dynamically during an evolution of the perforation channels within the thermal-mechanical interaction model.

9. The method of claim 1, wherein phase changes occurring in a melting and vaporization process are accounted for by latent heats of fusion and vaporization within the thermal-mechanical interaction model.

10. The method of claim 1, wherein a plastic mechanical behavior of the rock sample follows an arbitrary failure criterion that has a non-associated flow rule in shear yielding and follows an associated flow in tensile yielding according to:

$$f_s = \sigma_1 - \sigma_3 \frac{1+\sin\phi}{1-\sin\phi} + 2C_0\sqrt{\frac{1+\sin\phi}{1-\sin\phi}} \text{ and } f_t = \sigma_3 - \sigma_t,$$

wherein $f_s$ denotes a shear failure criterion; $\sigma_1$ is a maximum principal stress; $\sigma_3$ is a minimum principal stress; Ø is a friction angle; $C_0$ is a cohesive strength; $f_t$ is a tensile failure criterion; $\sigma_t$ is a tensile strength.

11. One or more non-transitory computer-readable storage media coupled to one or more processors and having instructions stored thereon which, when executed by the one or more processors, cause the one or more processors to perform operations comprising:
   receiving rock sample data regarding a rock sample from a drilling site; generating a thermal-mechanical interaction model based on the rock sample data, wherein the thermal-mechanical interaction model simulates heat transfer in the rock sample, wherein thermal energy propagates in a form of thermal conduction that is described in the thermal-mechanical interaction model according to a transient thermal conduction equation, and wherein the transient thermal conduction equation is described according to:

$$\rho C_V \frac{\partial T}{\partial t} = \nabla(k\nabla T) + q_V,$$

wherein:
   $\rho$ [kg/m$^3$] is the density of the rock sample; $C_v$ [J/(kg C)] is the specific heat of a constant volume of the rock sample; t[s] is time; T is the temperature [° C.]; k[W/(m ° C.)] is a thermal conductivity of the rock sample; and $q_V$ [W/m$^3$] is a volumetric heat-source intensity;
   generating a thermal-mechanical interaction model based on the rock sample data;
   determining, from the thermal-mechanical interaction model, a penetration rate and mechanical damage around perforation channels through modeling of heat emitted on an exposed surface of the rock sample by a laser beam emitted from a laser beam source; and
   evaluating an effectiveness of the laser beam source to be used in a perforation at the drilling site based on the determined penetration rate and mechanical damage.

12. The one or more non-transitory computer-readable storage media of claim 11, wherein the mechanical damage includes deformation and damage processes inside the rock sample.

13. The one or more non-transitory computer-readable storage media of claim 11, wherein the rock sample include uniformly distributed bedding planes with arbitrary dip direction and dip angle.

14. The one or more non-transitory computer-readable storage media of claim 11, wherein the operations further comprise:

determining temperature propagation, thermal expansion, and thermal-mechanical interaction through the modeling of the heat emitted on the exposed surface of the rock sample by the laser beam.

15. A computer-implemented system, comprising:

one or more processors; and a computer-readable storage device coupled to the one or more processors and having instructions stored thereon which, when executed by the one or more processors, cause the one or more processors to perform operations comprising:

receiving rock sample data regarding a rock sample from a drilling site; generating a thermal-mechanical interaction model based on the rock sample data, wherein the thermal-mechanical interaction model simulates heat transfer in the rock sample, wherein thermal energy propagates in a form of thermal conduction that is described in the thermal-mechanical interaction model according to a transient thermal conduction equation, and wherein the transient thermal conduction equation is described according to:

$$\rho C_V \frac{\partial T}{\partial t} = \nabla(k\nabla T) + q_V,$$

wherein:
$\rho$ [kg/m³] is the density of the rock sample; $C_v$ [J/(kg C)] is the specific heat of a constant volume of the rock sample; t[s] is time; T is the temperature [° C.]; k[W/(m ° C.)] is a thermal conductivity of the rock sample; and $q_V$ [W/m³] is a volumetric heat-source intensity;

generating a thermal-mechanical interaction model based on the rock sample data;

determining, from the thermal-mechanical interaction model, a penetration rate and mechanical damage around perforation channels through modeling of heat emitted on an exposed surface of the rock sample by a laser beam emitted from a laser beam source; and evaluating an effectiveness of the laser beam source to be used in a perforation at the drilling site based on the determined penetration rate and mechanical damage.

16. The computer-implemented system of claim 15, wherein a heating boundary is updated dynamically during an evolution of the perforation channels within the thermal-mechanical interaction model.

17. The computer-implemented system of claim 15, wherein phase changes occurring in a melting and vaporization process are accounted for by latent heats of fusion and vaporization within the thermal-mechanical interaction model.

* * * * *